March 2, 1954 E. A. MARMON Plant Pat. 1,260
ROSE PLANT
Filed Nov. 4, 1952
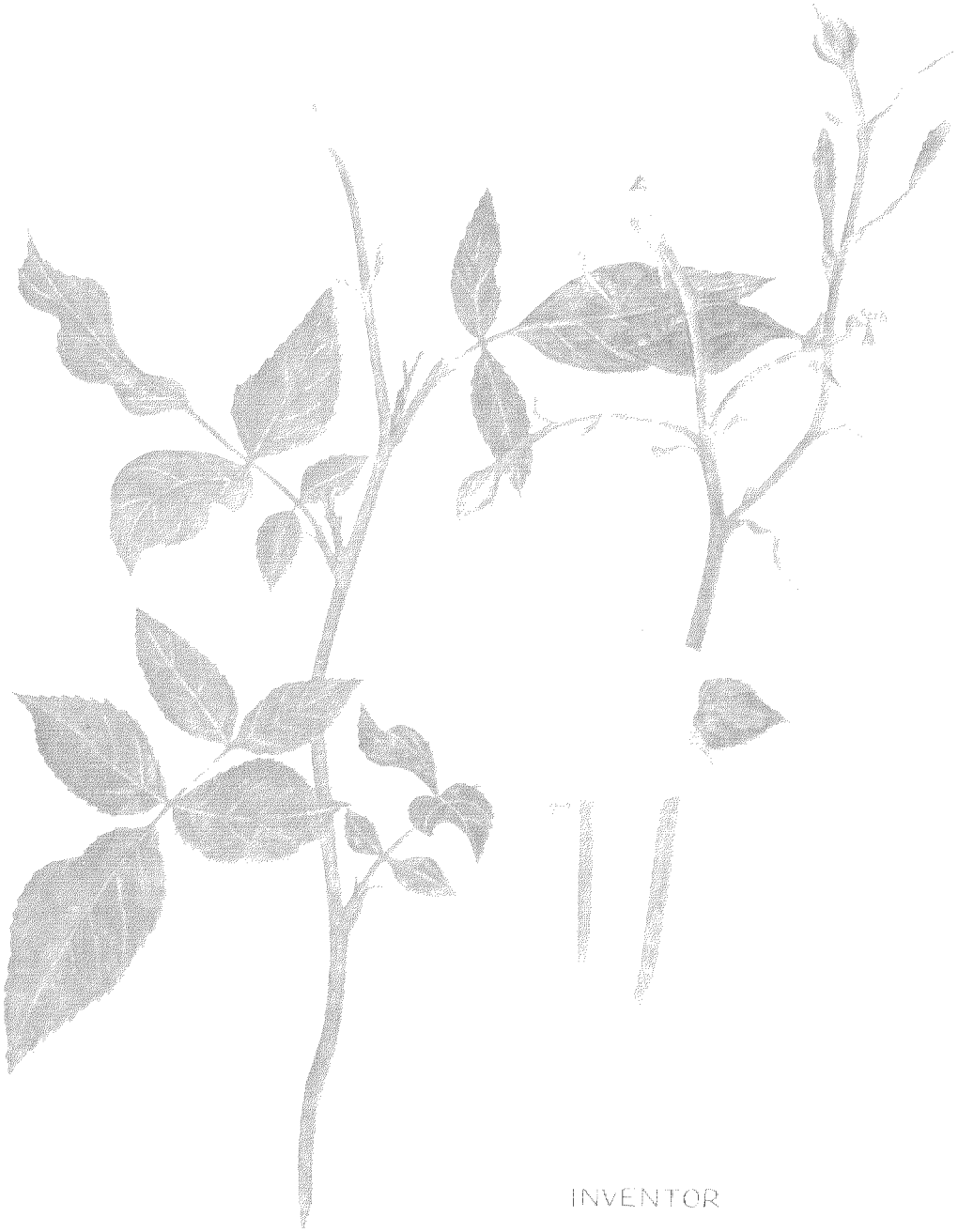
INVENTOR
Edwin A. Marmon
By Orville M. Kile
PLANT PATENT AGENT Patented Mar. 2, 1954 Plant Pat. 1,260

UNITED STATES PATENT OFFICE 1,260

ROSE PLANT

Edwin A. Marmon, Springfield, N. J., assignor to
Louis J. Marmon Co., Inc., Springfield, N. J.

Application November 3, 1952, Serial No. 318,540

1 Claim. (Cl. 47—61)

My present discovery pertains to a new variety of polyantha rose plant of the "floribunda or polyantha" type. The new variety originated as a cultivated sport of Garnette (unpatented) and was discovered by me in my nursery gardens in Springfield, N. J. The variety is much like its parent except for the color of the flower and its excellent keeping qualities.

This new variety has been asexually reproduced by me at the above-mentioned gardens by means of budding and is characteristics appear to be permanent.

Illustrations accompanying this specification are water color paintings which show in approximately their true colors typical flowers of my new variety in various stages of opening, together with some of the stems and foliage.

In the following detailed description, color plate references are to Ridgway's Color Standards and Nomenclature.

*The plant*

Growth: Vigorous, growing 3 or 4 feet in height. Bushy. Breaks freely.

Blooming habit: Prolific bloomer throughout the season.

Borne: Both singly and in clusters of 4 to 7.

Stems:

*Color.*—Approximately Grass Green (Plate VI).

*Strength.*—Slender, but strong and upright.

*Thorns.*—None on upper portion of stems. Numerous large sharp thorns, green and downward-pointing on lower portion of stem, and these are staggered in their position.

Foliage:

*Type.*—Pinnately compound, with terminal leaflet. Usually from 3 to 7 leaflets, but often single, narrow leaflets appear nearest flowers.

*Size.*—Terminal leaflet approximately 2 inches long and 1¼ inch wide.

*Shape.*—Oval, with acute apex. Base somewhat rounded. Margins sharply serrated.

*Texture.*—Very substantial.

*Color.*—New foliage red (approximately Dragon's Blood Red to Brick Red, Plate XIII). Older foliage dark green on upper surface (approximately Elm Green, Plate XVII).

*Rachis.*—Slender; grooved.

*Stipules.*—Slender; adnate; points sharp.

*The flower*

Bud:

*Borne.*—In axils of stems.

*Size.*—Green buds less than ½ inch long, with sepals hooded over top. When color is showing, but is approximately ¾ inch long.

*Shape.*—Pointed.

*Sepals.*—Relatively simple, only slightly branched; long; hooded over bud in early stages.

*Peduncle.*—Short; slender but strong.

*Opening.*—Very even.

Bloom:

*Size.*—Small to medium, best flowers being about 2 inches in diameter when fully expanded.

*Fragrance.*—None discernible.

*Petalage.*—Average 45 petals.

*Form.*—Very full, with depressed center at first. Outer row of petals smaller than next several rows. Opens high-centered, which form it retains, the stamens and pistils seldom visible except in the very last stages of opening.

*Longevity.*—Flower lasts exceptionally well, both on bush and as cut flower, excelling its parent in this respect.

*Color.*—White, slightly tinted with green. The outer petals generally show splotches of green, particularly notable when the flower is opening. Some specimens show a very slight touch or line of rose color on one of the petals of the flower.

Petals:

*Size.*—Largest petals measure approximately ⅞ inch in each direction.

*Shape.*—Outer petals are approximately round although sometimes crinkled when opening. Intermediate petals are spatulate and inner petals and petaloids twisted in the fully open flower. Margin usually somewhat ruffled.

*Persistence.*—Petals cling well.

*Arrangement.*—Imbricated and slightly reflexed.

*Texture.*—Substantial but not heavy.

Reproductive organs:

*Pistils.*—Many; fused; bunched in center of flower. Styles slender, greenish-white and uneven in length. Stigmas green to greenish-white.

*Stamens.*—Few; surround pistils. Filaments irregular in length; slender. Anthers large; light yellow.

*Pollen.*—Golden yellow.

Having thus disclosed my discovery, I claim:

The new and distinct variety of polyantha rose plant, substantially as herein shown and described and characterized as to novelty by the combination of its vigorous growth, prolific blooming habit and its long-keeping, essentially white bloom with tints of green.

EDWIN A. MARMON.

References Cited in the file of this patent

McFarland, "Modern Roses III," published 1947, pages 32 and 254.